United States Patent [19]

Meier et al.

[11] Patent Number: 5,340,855
[45] Date of Patent: Aug. 23, 1994

[54] N-METHYLATED BIS-4-PIPERIDYLPHOSPHITE

[75] Inventors: Hans R. Meier, Marly; Peter Hofmann, Basel, both of Switzerland

[73] Assignee: Ciba-Geigy Corporation, Ardsley, N.Y.

[21] Appl. No.: 63,999

[22] Filed: May 17, 1993

Related U.S. Application Data

[62] Division of Ser. No. 928,246, Aug. 10, 1992, Pat. No. 5,239,076.

[30] Foreign Application Priority Data

Aug. 13, 1991 [CH] Switzerland .................. 2383/91

[51] Int. Cl.$^5$ .................. C08K 5/3435; C08K 5/15
[52] U.S. Cl. .................. 524/102; 524/111; 252/400.21; 252/407
[58] Field of Search .................. 524/102, 111; 252/400.21, 407

[56] References Cited

U.S. PATENT DOCUMENTS

| | | | |
|---|---|---|---|
| 4,110,306 | 8/1978 | Minagawa et al. | 524/99 |
| 4,772,708 | 9/1988 | Di Battista et al. | 546/5 |
| 5,021,481 | 6/1991 | Galbo et al. | 524/99 |
| 5,039,723 | 8/1991 | Haruna et al. | 524/97 |

FOREIGN PATENT DOCUMENTS

| | | |
|---|---|---|
| 1513629 | 6/1978 | United Kingdom . |
| 2014586 | 8/1979 | United Kingdom . |

OTHER PUBLICATIONS

Methoden der Organischen Chemie (Houben-Weyl) Band X11/2 (1964).
Plastics Additives Handbook.
Chem. Abst. 91(20): 158608t, Hechenbleikner et al.

*Primary Examiner*—Kriellion S. Morgan
*Attorney, Agent, or Firm*—Luther A. R. Hall

[57] ABSTRACT

The invention relates to the novel compound 3,9-bis(1,2,2,6,6-pentamethyl-4-piperidyloxy)-2,4,8,10-tetraoxa-3,9-diphosphaspiro[5,5]undecane of formula I

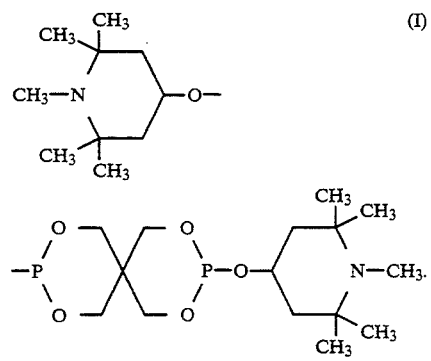

This compound can be used as stabilizer for organic material, especially as processing stabilizer for polyethylene and polypropylene.

10 Claims, No Drawings

N-METHYLATED BIS-4-PIPERIDYLPHOSPHITE

This application is a divisional of Ser. No. 07/928,246, filed Aug. 10, 1992, now U.S. Pat. No. 5,239,076.

The present invention relates to the novel compound 3,9-bis(1,2,2,6,6-pentamethyl-4-piperidyloxy)-2,4,8,10-tetraoxa-3,9-diphosphaspiro[5,5]undecane, to compositions containing said compound, and to the use thereof as stabiliser in organic material.

Organic phosphites and phosphonites are known in the art as co-stabilisers, secondary antioxidants and processing stabilisers, inter alia for polyolefins. Examples of such known phosphite stabilisers, including spiro-linked bisphosphites, will be found in R. Gächter/H. Müller (Ed.), Plastics Additives Handbook, 3rd Ed., p. 47, Hanser, Munich, 1990.

Hindered amines, including in particular compounds containing 2,2,6,6-tetramethylpiperidyl groups, are preferably used as hindered amine light stabilisers (HALS).

A great number of essentially unsymmetrical piperidylphosphites of the type

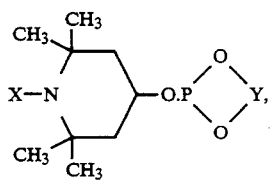

but bisphosphites as well, are disclosed in GB-A-1 513 629, including 3,9-bis(2,2,6,6-tetramethyl-4-piperidinyloxy)-2,4,8,10-tetraoxa-3,9-diphosphaspiro[5,5]undecane (Example 8 on page 7, lines 45–50; the nomenclature has been amended in accordance with IUPAC).

The use of 3,9-bis(2,2,6,6-tetramethyl-4-piperidinyloxy)-2,4,8,10-tetraoxa-3,9-diphosphaspiro[5,5]undecane for stabilising olefin polymers is also taught in GB-A-2 014 586.

The corresponding N-alkoxy-substituted bis-4-piperidylphosphites are disclosed in U.S. Pat. No. 5,021,481.

There still exists a need to provide effective stabilisers for organic materials which are susceptible to oxidative, thermal and/or light-induced degradation.

Surprisingly, it has now been found that a special bis-4-piperidylphosphite, namely the compound of formula I below, is a very suitable stabiliser for organic material. The suitability of this compound as processing stabiliser for synthetic polymers merits special mention.

In one of its aspects, the invention relates to the compound 3,9-bis( 1,2,2,6,6-pentamethyl-4-piperidyloxy)-2,4,8,10-tetraoxa-3,9-diphosphaspiro[5,5]undecane of formula I

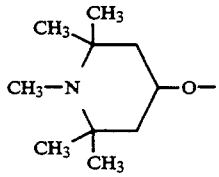

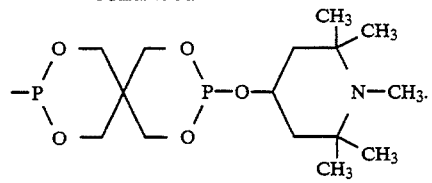

The compound of formula I can be prepared by starting from 3,9-dichloro-2,4,8,10-tetraoxa-3,9-diphosphaspiro[5,5]undecane, the synthesis of which is known and described, inter alia, in Houben-Weyl, 2nd Edition, Vol. XII/2, page 48, Thieme-Verlag, Stuttgart 1964. In this reaction, the starting compound is reacted with about two equivalents of 1,2,2,6,6-pentamethylpiperidin-4-ol in the presence of a suitable organic, polar or nonpolar, aprotic solvent. It is preferred to carry out this reaction in the presence of a base in the temperature range from 0° C. to the boiling point of the solvent.

Alternatively, it is possible to use the alcoholate derived from 1,2,2,6,6-pentamethylpiperidin-4-ol instead of the base.

Different amounts of the base can be used, ranging from catalytic amounts through stoichiometric amounts to the multiple molar excess over the piperidine derivative. The hydrogen chloride formed during the reaction may be converted by the base into the chloride, which can be removed by filtration and/or washing with a suitable aqueous or solid phase. In this procedure it is also possible to use a second, water-immiscible solvent. The product is conveniently purified by recrystallising the residue of the organic phase, which is concentrated or evaporated to dryness. The solvent used for the recrystallisation will typically be acetonitrile or hexane.

The solvents used for carrying out the condensation suitably include hydrocarbons (e.g. toluene, xylene, hexane, pentane or other petroleum ether fractions), halogensted hydrocarbons, (e.g. di- or trichloromethane, 1,2-dichloroethane, 1,1,1-trichloroethane), ethers (e.g. diethyl ether, dibutyl ether or tetrahydrofuran), and also acetonitrile, dimethyl formamide, dimethyl sulfoxide, N-methylpyrrolidone.

Suitable bases include tertiary amines (e.g. trimethylamine, triethylamine, tributylamine, N,N-dimethylaniline, N,N-diethylaniline or pyridine), hydrides (e.g. lithium, sodium, potassium hydride) or alcoholates (typically sodium methylate).

Hydrides, alkali metals, alkali metal hydroxides or sodium methylate can also be used to form the alcoholate of 1,2,2,6,6-pentamethylpiperidin-4-ol. The reaction product formed (e.g. water, methanol) is removed by distillation before the reaction with the chlorophosphite (e.g. as an azeotrope with toluene).

Further preparative methods start from suitable esters of low boiling alcohols or phenols or from suitable amides instead of from 3,9-dichloro-2,4,8,10-tetraoxa-3,9-diphosphaspiro[5,5]undecane. Thus 3,9-diethoxy-2,4,8,10-tetraoxa-3,9-diphosphaspiro[5,5]undecane or 3,9-bis(dimethylamino)-2,4,8,10-tetraoxa-3,9-diphosphaspiro[5,5]undecane can be used as starting compound in accordance with the general procedure described above. The reaction conditions must in this case be chosen such that the low boiling alcohol, or the phenol or amine, formed during the reaction is removed quantitatively by distillation (q.v. for example the analogous reaction described in GB-A-1 513 629).

The compound of formula I is admirably suitable for stabilising organic materials against light-induced, thermal and/or oxidative degradation. Accordingly, the invention also relates to compositions comprising (a) an organic material which is susceptible to oxidative, thermal and/or light-induced degradation, and (b) a compound of formula I.

Representative examples of such organic materials are:

1. Polymers of monoolefins and diolefins, typically polypropylene, polyisobutylene, polybut-1-ene, polymethylpent-1-ene, polyisoprene or polybutadiene, as well as polymers of cycloolefins, for example of cyclopentene or norbornene, polyethylene (which can be uncrosslinked or crosslinked), e.g. high density polyethylene (HDPE), low density polyethylene (LDPE), linear low density polyethylene (LLDPE), branched low density polyethylene (BLDPE).

2. Mixtures of the polymers mentioned in 1), typically mixtures of polypropylene with polyisobutylene, polypropylene with polyethylene (e.g. PP/HDPE, PP/LDPE) and mixtures of different types of polyethylene (e.g. LDPE/HDPE).

3. Copolymers of monoolefins and diolefins with each other or with other vinyl monomers, typically ethylene/propylene, linear low density polyethylene (LLDPE) and its mixtures with low density polyethylene (LDPE), propylene/but-1-ene, ethylene/hexene, ethylene/ethylpentene, ethylene/heptene, ethylene/octene, propylene/isobutylene, ethylene/but-1-ene, propylene/butadiene, isobutylene/isoprene, ethylene/alkyl acrylates, ethylene/alkyl methacrylates, ethylene/vinyl acetate copolymers or ethylene/acrylic acid copolymers and their salts (ionomers) and terpolymers of ethylene with propylene and a diene, e.g. hexadiene, dicyclopentadiene or ethylidene-norbornene; as well as mixtures with each other and with polymers mentioned in 1) above, e.g. polypropylene/ethylene-propylene-copolymers, LDPE/ethylene-vinyl acetate copolymers (EVA), LDPE/ethylene-acrylic acid copolymers (EAA), LLDPE/EVA, LLDPE/EAA and random or alternating polyalkylene/carbon monoxide-copolymers as well as mixtures thereof with other polymers, for example polyamides.

3a. Hydrocarbon resins (e.g. $C_5$–$C_9$) and hydrogenated modifications thereof (e.g. tackifiers) and mixtures of polyalkylenes and starch.

4. Polystyrene, poly(p-methylstyrene), poly(α-methylstyrene).

5. Copolymers of styrene or α-methylstyrene with dienes or acrylic derivatives, typically styrene/butadiene, styrene/acrylonitrile, styrene/alkyl methacrylate, styrene/maleic anhydride, styrene/butadiene/alkyl acrylate, styrene/butadiene/alkyl methacrylate, styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, typically styrene/butadiene/styrene, styrene/isoprene/styrene, styrene/ethylene/butylene/styrene or styrene/ethylene/propylene/styrene.

6. Graft copolymers of styrene or α-methylstyrene, typically styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed in 5), e.g. the copolymer mixtures known as ABS, MBS, ASA or AES polymers.

7. Halogen-containing polymers, typically polychloroprene, chlorinated rubbers, chlorinated or sulfochlorinated polyethylene, copolymers of ethylene and chlorinated ethylene, epichlorohydrin homo- and copolymers, polymers of halogenated vinyl compounds, e.g. polyvinyl chloride, polyvinylidene chloride, polyvinyl fluoride, polyvinylidene fluoride, as well as copolymers thereof, typically vinyl chloride/vinylidene chloride, vinyl chloride/vinyl acetate or vinylidene chloride/vinyl acetate copolymers.

8. Polymers derived from α,β-unsaturated acids and derivatives thereof, e.g. polyacrylates and polymethacrylates, polymethyl methacrylate impact-modified with butyl acrylate, polyacrylamides and polyacrylonitrile.

9. Copolymers of the monomers mentioned in 8) with each other or with other unsaturated monomers, for example acrylonitrile/butadiene, acrylonitrile/alkyl acrylate, acrylonitrile/alkoxyalkyl acrylate or acrylonitrile/vinyl halide copolymers or acrylonitrile/ alkyl methacrylate/butadiene terpolymers.

10. Polymers derived from unsaturated alcohols and amines, or acyl derivatives thereof or acetals thereof, typically polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, typically polyalkylene glycols, polyethylene oxide, polypropylene oxide or copolymers thereof with bisglycidyl ethers.

12. Polyacetals such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes derived from polyethers, polyesters or hydroxyl-terminated polybutadienes on the one hand and aliphatic or aromatic polyisocyanates on the other, as well as precursors thereof.

15. Polyamides and copolyamides derived from diamines and dicarboxylic acids and/or from aminocarboxylic acids or the corresponding lactams, e.g. polyamide 4, polyamide 6, polyamide 6/6, 6/10, 6/9, 6/12, 4/6, 12/12, polyamide 11, polyamide 12, aromatic polyamides obtained by condensation of m-xylene, diamine and adipic acid; polyamides prepared from hexamethylenediamine and isophthalic acid and/or terephthalic acid and optionally an elastomer as modifier, e.g. poly(2,4,4,-trimethylhexamethylene) terephthalamide or poly-m-phenylene isophthalamide; and also copolymers of the aforementioned polyamides with polyolefins, olefin copolymers, ionomers or chemically bonded or grafted elastomers; or with polyethers, as with polyethylene glycols, polypropylene glycols or polytetramethylene glycols; polyamides or copolyamides modified with EPDM or ABS; polyamides condensed during processing (RIM polyamide systems).

16. Polyureas, polyimides, polyamide-imides and polybenzimidazoles.

17. Polyesters derived from dicarboxylic acids and diols and/or from hydroxycarboxylic acids or the corresponding lactones, e.g. polyethylene terephthalate, polybutylene terephthalate, poly-1,4-dimethylolcyclohexane terephthalate, poly[2,2-(4-hydroxyphenyl)-propane]terephthalate and polyhydroxybenzoates as well as block-copolyether-esters derived from hydroxyl-terminated polyethers 18. Polycarbonates and polyester carbonates.

19. Polysulfones, polyether sulfones and polyether ketones.

20. Crosslinked polymers which are derived from aldehydes on the one hand and phenols, ureas and melamines on the other, e.g. phenol/formaldehyde resins, urea/formaldehyde resins and reelamine/formaldehyde resins.

21. Drying and non-drying alkyd resins.

22. Unsaturated polyester resins derived from copolyesters of saturated and unsaturated dicarboxylic acids with polyhydric alcohols and vinyl compounds as crosslinking agents, and also halogenated modifications thereof of low flammability.

23. Crosslinkable acrylic resins derived from substituted acrylic esters, e.g. epoxy acrylates, urethane acrylates or polyester acrylates.

24. Alkyd resins, polyester resins or acrylate resins which are crosslinked with melamine resins, urea resins, polyisocyanates or epoxy resins.

25. Crosslinked epoxy resins which are derived from polyepoxides, typically from bisglycidyl ethers or from cycloaliphatic diepoxides.

26. Natural polymers, such as cellulose, rubber, gelatin and chemically modified homologous derivatives thereof, e.g. cellulose acetates, cellulose propionates and cellulose butyrates, or the cellulose ethers, typically methyl cellulose; rosins and their derivatives.

27. Mixtures of polymers as mentioned above, typically PP/EPDM, polyamide EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, typically mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios which are used as textile spinning compositions, as well as aqueous emulsions of such materials.

29. Aqueous emulsions of natural or synthetic rubber, e.g. natural latex or latices of carboxylated styrene/-butadiene copolymers.

The invention further relates to compositions which comprise, as component (a), natural, semi-synthetic or synthetic polymers which are susceptible to oxidative, thermal and/or light-induced degradation, especially thermoplastic polymers, preferably polyolefins, most preferably polyethylene or polypropylene.

The invention also relates to the use of the compound of formula I for stabilising organic material against oxidative, thermal and/or actinic degradation, in particular as processing stabiliser (heat stabiliser) in thermoplastic polymers.

The organic materials to be protected are preferably natural, semi-synthetic or, more particularly, synthetic organic materials. Especially preferred organic materials are thermoplastic polymers, preferably PVC or polyolefins, most preferably polyethylene and polypropylene (PP).

The compositions of this invention conveniently contain the compound of formula I in an amount of 0.01 to 10, typically 0.05 to 5, preferably 0.05 to 3 and, most preferably, 0.05 to 1% by weight. The percentages by weight are based on the total amount of said compound. The computation is based on the total weight of the organic material without the compound of formula I.

Incorporation in the organic materials can be effected by blending them with, or by applying thereto, the compound of formula I and further optional additives by methods which are commonly used in the art. If the organic materials are polymers, especially synthetic polymers, the incorporation can be effected before or during the fabrication of shaped articles or by applying the dissolved or dispersed compound to the polymer, with or without subsequent evaporation of the solvent. In the case of elastomers, these may also be stabilised as lattices. A further means of blending the compound of formula I into polymers consists in adding said compound before, during or directly after the polymerisation of the corresponding monomers or before crosslinking. The compound of formula I can also be added in encapsulated form (e.g. in waxes, oils or polymers). If the compound of formula I is added before or during polymerisation, it can also act as regulator for the chain length of the polymers (chain terminator).

The compound of formula I can also be added in the form of a masterbatch which contains this compound to the polymers to be stabilised, typically in a concentration of 2.5 to 25% by weight.

The compound of formula I may conveniently be incorporated by the following techniques:
- as emulsion or dispersion (e.g. to lattices or emulsion polymers),
- as dry mixture while blending additional components or polymer mixtures
- by direct addition to the processing apparatus (e.g. extruder, internal mixer and the like)
- as solution or melt.

Polymer compositions of this invention can be used in different form and processed to different products, including sheets, filaments, ribbons, moulded articles, profiles or as binders for paints and varnishes, adhesives or putties.

As already mentioned, the organic materials to be protected are preferably natural, semi-synthetic or, more particularly, synthetic polymers. It is especially useful to protect thermoplastic resins, preferably polyolefins. In this connection, the excellent action of the compound of formula I as processing stabiliser (heat stabiliser) is to be singled out for special mention. To this end, the compound of formula I is conveniently added before or during the processing of the polymer. It is, however, also possible to stabilise other polymers (e.g. elastomers) or lubricants and hydraulic fluids against degradation, such as light-induced and/or thermal oxidative degradation. Examples of elastomers will be found among the above list of possible organic materials.

The suitable lubricants and hydraulic fluids may be based on mineral or synthetic oils or mixtures thereof. The lubricants are known to the skilled person and described in the pertinent technical literature, for example in Dieter Klamann, "Schmierstoffe und verwandte Produkte" (Lubricants and Related Products), Verlag Chemie, Weinheim, 1982, in Schewe-Kobek, "Das Schmiermittel-Taschenbuch" (The Lubricant Handbook), Dr. Alfred Hüthig-Verlag, Heidelberg, 1974) and in "Ullmanns Enzyklopädie der technischen Chemie", (Encyclopedia of Industrial Chemistry), Vol. 13, pages 85–94 (Verlag Chemie, Weinheim, 1977).

The invention further relates to a process for protecting organic material against oxidative, thermal and/or actinic degradation, which comprises incorporating in, or applying to, said material the compound of formula I as stabiliser.

In addition to containing the novel compound, the compositions of the invention, especially if they contain organic, preferably synthetic, polymers, may contain other conventional additives.

Illustrative examples of such further additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methylundec-1'-yl)-phenol, 2,4-dimethyl-6-(1'-methylheptadec-1'-yl)-phenol, 2,4-dimethyl-6-(1'-methyltridec-1'-yl)-phenol and mixtures thereof.

1.2. Alkylthiomethylphenols, for example 2,4-di-octylthiomethyl-6-tert-butylphenol, 2,4-di-octylthiomethyl-6-methylphenol, 2,4-di-octylthiomethyl-6-ethylphenol, 2,6-di-do-decylthiomethyl-4-nonylphenol.

1.3. Hydroquinones and alkylated hydroquinones, for example 2,6-di-tert-butyl-4-methoxyphenol, 2,5-di-tert-butyl-hydroquinone, 2,5-di-tert-amyl-hydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenylstearate, bis(3,5-di-tert-butyl-4-hydroxyphenyl)adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.5. Alkylidene bisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethyl-benzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2(3'-tert-butyl-2'-hydroxy-5'-methyl-benzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.6. O—, N— and S-benzyl compounds, for example 3,5,3',5'-tetra-tert-butyl-4,4'-dihydroxydibenzyl ether, octadecyl-4-hydroxy-3,5-dimethylbenzyl mercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzyl mercaptoacetate.

1.7. Hydroxybenzylated malonates, for example dioctadecyl-2,2-bis(3,5-di-tert-butyl-2-hydroxybenzyl)-malonate, dioctadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)-phenyl]-2,2-bis(3,5-di-tert-butyl-4-hydroxybenzyl)malonate.

1.8. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine compounds, for example 2,4-bisoctylmercapto-6-(3,5-di-tert-butyl-4-hydroxyanilino)-1,3,5-triazine, 2-octylmercapto-4,6-bis(3,5-di-tert-butyl-4-hydroxy-anilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl )isocyanurate.

1.10. Benzyl phosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of monoethyl 3,5-di-tert-butyl-4-hydroxybenzylphosphonate.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)-propionic acid with mono- or polyhydric alcohols, for example methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, for example methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(3,5-dicyclohexyl-4-hydroxyphenyl)propionic acid with mono- or polyhydric alcohols, for example methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of 3,5-di-tert-butyl-4-hydroxyphenylacetic acid with mono- or polyhydric alcohols, for example methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl)propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV Absorbers and Light-Stabilisers 2.1.2-(2'-hydroxyphenyl)-benzotriazoles, for example 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, 3',5'-di-tert-amyl-, 3',5'-bis-(α,α-dimethylbenzyl)-, mixture of 5-chloro-3'-tert-butyl-5'-(2-octyloxycarbonylethyl)- and 5-chloro-3'-tert-butyl-5'-[2-(2-ethylhexyloxy)-carbonylethyl]-, 5-chloro-3'-tert-butyl-5'-(2-methoxycarbonylethyl)-, 3'-tert-butyl-5'-(2-methoxycarbonylethyl)-, 3'-tert-butyl-5'-(2-octyloxycarbonylethyl)-, 3'-tert-butyl-5'-[2-(2-ethylhexyloxy)-carbonylethyl]-, 3'-dodecyl-5'-methyl- and 3'-tert-butyl-5'-(2-isooctyloxycarbonylethyl)-2'-hydroxyphenyl-2H-benzotriazole(2), 2,2'-methylene-bis[4-(1,1,3,3-tetramethylbutyl)-6-benzotriazol-2-ylphenol]; transesterification product of 2-[3'-tert-butyl-5'-(2-methoxycarbonylethyl)-2'-hydroxy-phenyl]-2H-benzotriazole with polyethylene glycol 300;

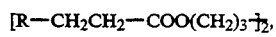

wherein R=3'-tert-butyl-4'-hydroxy-5'-2H-benzotriazol-2-ylphenyl.

2.2.2-hydroxybenzophenones, for example the 4-hydroxy, 4-methoxy, 4-octyloxy, 4-decyloxy, 4-dodecyloxy, 4-benzyloxy, 4,2',4'-trihydroxy or 2'-hydroxy-4,4'-dimethoxy derivative.

2.3. Esters of unsubstituted or substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, the 2,4-di-tert-butylphenyl ester of 3,5-di-tert-butyl-4-hydroxybenzoic acid, the hexadecyl ester of 3,5-di-tert-butyl-4-hydroxybenzoic acid, the octadecyl ester of 3,5-di-tert-butyl-4-hydroxybenzoic acid, the 2-methyl-4,6-di-tert-butylphenyl ester of 3,5-di-tert-butyl-4-hydroxybenzoic acid.

2.4. Acrylates, for example ethyl α-cyano-β,β-diphenylacrylate, isooctyl α-cyano-β,β-diphenylacrylate, methyl α-carbomethoxycinnamate, methyl α-cyano-β -methyl-p-methoxycinnamate or butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], e.g. the 1: 1 or the 1:2 complex, with or without additional ligands, typically n-butylamine, triethanolamine or N-cyclohexyl-diethanolamine, nickel dibutyl dithiocarbamate, nickel salts of monoalkyl esters, typically the methyl or ethyl ester, of 4-hydroxy-3,5-di-tert-butyl benzyl phosphonic acid, nickel complexes of ketoximes, e.g. 2-hydroxy-4-methylphenylundecyl ketoxime, nickel complexes of 1-phenyl-4-lauroyl-5-hydroxy-pyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis( 1,2,2,6,6-pentamethyl-piperidyl)sebacate, n-butyl-3,5-di-tert-butyl-4-hydroxybenzyl-malonic acid bis(1,2,2,6,6-pentamethylpiperidyl) ester, the condensate of 1-hydroxyethyl-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butyl benzyl)malonate, 3-n-octyl-7,7,9,9-tetramethyl-1,3,8-triazaspiro[4.5]-decane-2,4-dione, bis(1-octyloxy-2,2,6,6-tetramethylpiperidyl)sebacate, bis( 1-octyloxy-2,2,6,6-tetramethylpiperidyl)succinate, the condensate of N,N'-bis(2,2,6,6-tetramethyl-4-piperidyl)hexamethylenediamine and 4-morpholino-2,6-dichloro-1,3,5-triazine, the condensate of 2-chloro-4,6-di-(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)-pyrrolidine-2,5-dione, 3-dodecyl-1-( 1,2,2,6,6-pentamethyl-4-piperidyl )pyrrolidine-2,5-dione.

2.7. Oxamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and a mixture thereof with 2-ethoxy-2'-ethyl-5,4'-di-tert-butoxanilide, mixtures of o- and p-methoxy-disubstituted and of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propoxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-hydroxy-4-dodecyloxyphenyl)-4,6-bis(2,4-dimethylphenyl)-1,3,5-triazine, 2-[2-hydroxy-4-(2-hydroxy-3-butoxypropoxy)phenyl]-4,6-bis(2,4-dimethylphenyl)-1,3,5-triazine, 2-[2-hydroxy-4-(2-hydroxy-3-octyloxypropoxy)phenyl]-4,6-bis(2,4-dimethylphenyl)-1,3,5-triazine.

3. Metal deactivators, for example N,N'-diphenyloxamide, N-salicylal-N'-salicyloylhydrazine, N,N'-bis(-salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic acid dihydrazide, oxanilide, isophthalic acid dihydrazide, sebacic acid bisphenylhydrazide, N,N'-diacetaladipic acid dihydrazide, N,N'-bis(salicyloyl)oxalic acid dihydrazide, N,N'-bis(salicyloyl)thiopropionic acid dihydrazide.

4. Phosphites and phosphonites, for example triphenyl phosphite, diphenylalkyl phosphites, phenyldialkyl phosphites, tris(nonylphenyl)phosphite, trilauryl phosphite, trioctadecyl phosphite, distearylpentaerythritol diphosphite, tris(2,4-di-tert-butylphenyl)phosphite, diisodecylpentaerythritol diphosphite, bis(2,4-di-tert-butylphenyl)pentaerythritol diphosphite, bis(2,6-di-tert-butyl-4-methylphenyl)pentaerythritol diphosphite, bisisodecyloxypentaerythritol diphosphite, bis(2,4-di-tert-butyl-6-methylphenyl)pentaerythritol diphosphite, bis(2,4,6-tri-tert-butylphenyl)pentaerythritol diphosphite, tristearylsorbitol triphosphite, tetrakis(2,4-di-tert-butylphenyl)-4,4'-biphenylene diphosphonite, 6-isooctyloxy-2,4,8,10-tetra-tert-butyl-12H-dibenz[d,g]-1,3,2-dioxaphosphocine, 6-fluoro-2,4,8,10-tetra-tert-butyl-12-methyl-dibenz[d,g]-1,3,2-dioxaphosphocine.

5. Peroxide scavengers, for example esters, typically the lauryl, stearyl, myristyl or tridecyl ester, of β-thiodipropionic acid, mercaptobenzimidazole, the zinc salt of 2-mercaptobenzimidazole, zinc dibutyl dithiocarbamate, dioctadecyl disulfide, pentaerythritol tetrakis(β-dodecylmercapto)propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal and alkaline earth metal salts of higher fatty acids, typically calcium stearate, zinc stearate, magnesium behenate, magnesium stearate, sodium ricinoleate, potassium palmitate, antimony pyrocatecholate or stannic pyrocatecholate.

8. Nucleating agents, for example 4-tert-butylbenzoic acid, adipic acid, diphenylacetic acid.

9. Fillers and thickeners, for example calcium carbonate, silicates, glass fibres, asbestos, talcum, kaolin, mica, barium sulfate, metal oxides and hydroxides, carbon black, graphite.

10. Other additives, for example plasticisers, lubricants, emulsifiers, pigments, optical brighteners, flame-retardants, antistatic agents, blowing agents.

11. Benzofuranones or indolinones.

In addition to comprising component (a) and the compound of formula (1), other preferred compositions comprise still further additives, especially phenolic antioxidants, light stabilisers and/or processing stabilisers.

Especially preferred further additives (stabilisers) are the benzofuran-2-ones disclosed, inter alia, in WO-A 80/01566 and EP-A 415 887.

Representative examples of such benzofuran-2-ones are compounds of formula $$\begin{array}{c} R_5 \\ R_4 \\ R_3 \\ R_2 \quad H \quad R_1 \end{array} \quad \text{C=O,}$$

wherein $R_1$ is phenyl or phenyl which is substituted by 1 to 3 alkyl radicals together containing not more than 18 carbon atoms, alkoxy of 1 to 12 carbon atoms, alkoxycarbonyl of 2 to 18 carbon atoms or chloro;

$R_2$ is hydrogen;

$R_4$ is hydrogen, alkyl of 1 to 12 carbon atoms, cyclopentyl, cyclohexyl or chloro;

$R_3$ has the meaning of $R_2$ or $R_4$ or is a radical of formula $$-(CH_2)_n\overset{O}{\underset{\|}{C}}-OR_6, \quad -(CH_2)_n\overset{O}{\underset{\|}{C}}-N(R_7)_2,$$

$$+CH_2)_n\overset{O}{\underset{\|}{C}}-O-A-O-\overset{O}{\underset{\|}{C}}+CH_2)_nE,$$

$$+CH_2)_n\overset{O}{\underset{\|}{C}}-NR_8-A-NR_8-\overset{O}{\underset{\|}{C}}+CH_2)_nE,$$

$$+CH_2)_n\overset{O}{\underset{\|}{C}}-NR_8-A-O-\overset{O}{\underset{\|}{C}}+CH_2)_nE,$$

$$+CH_2)_n\overset{O}{\underset{\|}{C}}-N\underset{\diagup\diagdown}{\phantom{XX}}N-\overset{O}{\underset{\|}{C}}+CH_2)_nE,$$

$$-CH_2-S-R_9, \quad -CH(C_6H_5)-\overset{O}{\underset{\|}{C}}-OR_6$$

or —D—E, wherein $R_6$ is hydrogen, alkyl of 1 to 18 carbon atoms, alkyl of 2 to 18 carbon atoms which is interrupted by oxygen or sulfur, dialkylaminoalkyl containing a total of 3 to 16 carbon atoms, cyclopentyl, cyclohexyl, phenyl or phenyl which is substituted by 1 to 3 alkyl radicals together containing not more than 18 carbon atoms;

n is 0, 1 or 2;

the substituents $R_7$ are each independently of the other hydrogen, alkyl of 1 to 18 carbon atoms, cyclopentyl, cyclohexyl, phenyl, phenyl which is substituted by 1 or 2 alkyl radicals which together contain not more than 16 carbon atoms, a radical of formula

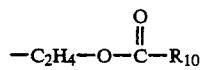

or, together with the linking nitrogen atom, they form a piperidino or morpholino radical;
m is 1 to 18;
$R_{10}$ is hydrogen, alkyl of 1 to 22 carbon atoms or cycloalkyl containing 5 to 12 carbon atoms;
A is alkylene of 2 to 6 carbon atoms which may be interrupted by nitrogen, oxygen or sulfur;
$R_8$ is hydrogen, alkyl of 1 to 18 carbon atoms, cyclopentyl, cyclohexyl, phenyl, phenyl which is substituted by 1 or 2 alkyl radicals together containing not more than 16 carbon atoms or benzyl;
$R_9$ is alkyl of 1 to 18 carbon atoms;
D is —O—, —S—, —SO—, —SO$_2$—, or —C($R_{11}$)$_2$—;
the substituents $R_{11}$ are each independently of the other hydrogen, alkyl which together contains not more than 16 carbon atoms, phenyl or a radical of formula

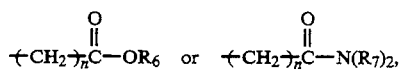

wherein n, $R_6$ and $R_7$ have the given meanings;
E is a radical of formula

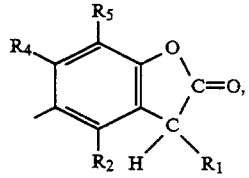

wherein $R_1$, $R_2$ and $R_4$ have the given meanings; and $R_5$ is hydrogen, alkyl of 1 to 20 carbon atoms, cyclopentyl, cyclohexyl, chloro or a radical of formula

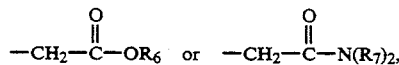

wherein $R_6$ and $R_7$ have the given meanings, or $R_5$ together with $R_4$ form a tetramethylene radical.

Preferred benzofuran-2-ones are those wherein $R_3$ is hydrogen, alkyl of 1 to 12 carbon atoms, cyclopentyl, cyclohexyl, chloro or a radical of formula

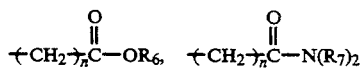

or —D—E, wherein n, $R_6$, $R_7$, D and E are as defined above, and $R_6$ is preferably hydrogen, alkyl of 1 to 18 carbon atoms, cyclopentyl or cyclohexyl.

Further preferred benzofuran-2-ones are those wherein $R_1$ is phenyl or phenyl which is substituted by 1 or 2 alkyl radicals together containing not more than 12 carbon atoms; $R_2$ is hydrogen; $R_4$ is hydrogen or alkyl of 1 to 12 carbon atoms; $R_3$ is hydrogen, alkyl of 1 to 12 carbon atoms,

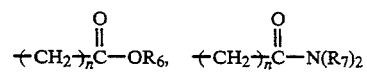

or —D—E; $R_5$ is hydrogen,
alkyl of 1 to 20 carbon atoms,

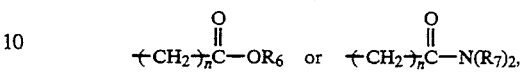

or $R_5$ together with $R_4$ form a tetramethylene radical, and n, $R_6$, $R_7$, D and E are as defined at the outset.

Particularly interesting benzofuran-2-ones are also those wherein $R_t$ is phenyl; $R_3$ is hydrogen, alkyl of 1 to 12 carbon atoms, or —D—E; $R_2$ and $R_4$ are each independently of the other hydrogen or alkyl of 1 to 4 carbon atoms; and $R_5$ is alkyl of 1 to 20 carbon atoms, and D and E are as defined at the outset.

Finally, benzofuran-2-ones which merit very particular interest are those wherein $R_1$ is phenyl; $R_3$ is alkyl of 1 to 4 carbon atoms or —D—E; $R_2$ and $R_4$ are hydrogen; and $R_5$ is alkyl of 1 to 4 carbon atoms, cyclopentyl or cyclohexyl, and D is —C($R_{11}$)$_2$— and E is a radical of formula

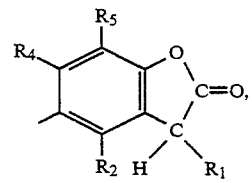

in which formulae the substituents $R_{11}$ are identical or different from each other and are each alkyl of 1 to 4 carbon atoms, and $R_1$, $R_2$, $R_4$ and $R_5$ have the given meanings.

The amount of additional additives, especially stabilisers, including the cited benzofuran-2-ones, can vary over a wide range. They may be present in the inventive compositions typically in amounts of 0.005 to 10% by weight, preferably 0.01 to 5% by weight, most preferably 0.05 to 2% by weight.

The following Examples illustrate the preparation and use of the inventive compound. Unless otherwise indicated, percentages are by weight.

Preparation of
3,9-bis(1,2,2,6,6-pentamethyl-4-piperidyloxy)-2,4,8,10-tetraoxa-3,9-diphosphaspiro[5,5]undecane A solution of 553 g (3.2 mol) of 1,2,2,6,6-pentamethylpiperidin-4-ol in 789.8 g (7.8 mol) of triethylamine and 500 ml of toluene is added dropwise at 60° C. to a solution of 344 g (1.3 mol) of 3,9-dichloro-2,4,8,10-tetraoxa-3,9-diphosphaspiro[5,5]undecane in 450 ml of toluene. The temperature rises to 93° C. The reaction mixture is refluxed for 22 hours and filtered over silica gel. The filtrate is evaporated to dryness.

A portion (350 g) of the residue (716 g) is taken up in toluene and the solution is washed with water and 0.1 molar HCl. The solvent is then removed and the residue of the organic phase (290 g) is recrystallised from 400 ml of hexane, giving 201 g of the title compound with a melting point of 106° C.

The second portion of the unpurified residue is taken in toluene, and the solution is washed with water and freed from solvent. The residue of the organic phase is then recrystallised from 700 ml of acetonitrile, giving 240.7 g of the title compound with a melting point of 106° C.

Recrystallisation of the residue of the combined mother liquors (162.7 g) from 200 ml of acetonitrile gives a further 75.4 g of product with a melting point of 106° C.

The total yield is 74.4%.

Use Example 1: Stabilisation of Polypropylene 1.3 kg of polypropylene powder (melt index 3.2 g/10 min, measured at 230° C./2.16 kg) are blended with 0.05% of calcium stearate, 0.05% of tetrakis(3,5-di-tert-butyl-4-hydroxyphenylpropionyloxymethyl)methane and 0.05% and 0.1% of the novel bisphosphite (compound of formula I). This blend is extruded at 100 rpm in an extruder having a cylinder diameter of 20 mm and a length of 400 mm, the three heating zones being adjusted to 260° C., 270° C. and 280° C. respectively. The extrudate is cooled by drawing it through a water bath and then granulated. The granulate is extruded a further four times. After the 1st, 3rd and 5th extrusion, the melt index is measured at 230° C./2.16 kg. The results are reported in Table 1.

TABLE 1

| Melt index of polypropylene after 1, 3 and 5 extrusions at 230° C. | | | |
|---|---|---|---|
| concentration of the bisphosphite | 0.1% | 0.05% | without phosphite |
| Melt index after | | | |
| 1st extrusion | 2.3 | 2.4 | 8 |
| 3rd extrusion | 2.9 | 3.1 | 15 |
| 5th extrusion (in g/10 min) | 4.0 | 4.4 | 27 |

The increase in the melt index with the number of passes shows that the polypropylene chains are cleaved by the stress during extrusion. The melt index rises sharply when no biphosphite is added. Addition of the novel compound greatly reduces this increase in the melt index and thus damage to the polypropylene.

Use Example 2: Stabilisation of High Density Polyethylene 1.3 kg of high density polyethylene (d=0.940 g/cm$^3$), prepared with a chromium catalyst, are blended with the amounts of Irganox 1076®(3,5-di-tert-butyl-4-hydroxyphenylpropionyloxyoctadecane) and of the compound of formula I indicated in Tables 2-4.

Before extrusion the polyethylene has a melt index of 3.0 g/10 min, measured at 190° C./5 kg, and a melt index of 48.1 g/10 min, measured at 190° C./21.6 kg. High density polyethylene, prepared using a chromium catalyst, crosslinks in an undesirable manner during extrusion. This crosslinking is observed in a decrease in the melt index.

The blends are extruded at 100 rpm in an extruder having a cylinder diameter of 20 mm and a length of 400 mm, the three heating zones being adjusted to 240° C., 250° C. and 260° C. respectively. The extrudate is cooled by drawing it through a water bath and then granulated. The granulate is extruded a further four times. After the 3rd and 5th extrusion, the melt indices are measured at 190° C./5 kg and at 190° C./21.6 kg. For comparison purposes, a test is additionally carried out without the novel stabiliser and a further test entirely without additives, i.e. without the novel stabiliser and without Irganox 1076®. The results are reported in Tables 2 and 3. Table 4 shows additionally the ratio of the two melt indices MFI(21.6 kg)/MFI(5 kg) measured at 190° C.

TABLE 2

| Melt index at 190° C./21.6 kg (in g/10 min) | | | | |
|---|---|---|---|---|
| Concentration: | | | | |
| Compound of formula I | 0.10% | 0.13% | without | without |
| Irganox 1076 ® | 0.05% | 0.02% | 0.15% | without |
| Melt index | | | | |
| before 1st extrusion | 48.1 | 48.1 | 48.1 | 48.1 |
| after 3rd extrusion | 42.3 | 42.4 | 40.9 | 29.2 |
| after 5th extrusion | 41.1 | 40.9 | 38.9 | 23.3 |

TABLE 3

| Melt index at 190° C./5 kg (in g/10 min) | | | | |
|---|---|---|---|---|
| Concentration: | | | | |
| Compound of formula I | 0.10% | 0.13% | without | without |
| Irganox 1076 ® | 0.05% | 0.02% | 0.15% | without |
| Melt index | | | | |
| before 1st extrusion | 3.0 | 3.0 | 3.0 | 3.0 |
| after 3rd extrusion | 2.4 | 2.5 | 2.0 | 0.7 |
| after 5th extrusion | 2.2 | 2.2 | 1.6 | 0.4 |

TABLE 4

| Melt index ratio MFI(21.6 kg)/MFI(5 kg) measured at 190° C. | | | | |
|---|---|---|---|---|
| Concentration: | | | | |
| Compound of formula I | 0.10% | 0.13% | without | without |
| Irganox 1076 ® | 0.05% | 0.02% | 0.15% | without |
| Melt index | | | | |
| before 1st extrusion | 16.0 | 16.0 | 16.0 | 16.0 |
| after 3rd extrusion | 17.6 | 16.9 | 20.5 | 41.7 |
| after 5th extrusion | 18.7 | 18.5 | 24.3 | 58.2 |

Tables 2 and 3 show higher melt indices when the novel stabiliser is used. This corresponds to a lower degree of undesirable crosslinking during the processing of the polyethylene.

The melt index ratio shown in Table 4 is obtained by dividing the melt index measured at 21.6 kg (Table 2) by the corresponding value measured at 5 kg (Table 3). This ratio is large if the molecular weight distribution is broad. The ratio of the melt indices is small if the molecular weight distribution is narrow. The addition of the stabilisers is intended to counteract a broadening of the molecular weight distribution during processing. The results reported in Table 4 show that the novel biphosphite acts in the desired manner.

What is claimed is:

1. A stabilized composition which comprises
   (a) an organic material which is susceptible to oxidative, thermal or light-induced degradation, and
   (b) an effective stabilizing amount of the compound of formula I

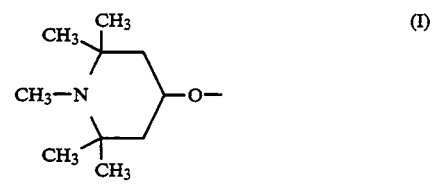

-continued

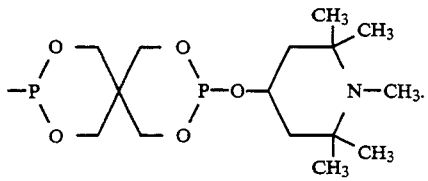

2. A composition according to claim 1, which comprises additional further additives besides components (a) and (b).

3. A composition according to claim 2, which comprises phenolic antioxidants, light stabilisers and/or processing stabilisers as further additives.

4. A composition according to claim 3, which comprises at least one compound of the benzofuran-2-one type as further additive.

5. A composition according to claim 1, wherein component (a) is selected from natural, semi-synthetic or synthetic polymers.

6. A composition according to claim 5, wherein component (a) is a thermoplastic polymer.

7. A composition according to claim 6, wherein component (a) is a polyolefin.

8. A composition according to claim 7, wherein component (a) is a polyethylene or polypropylene.

9. A process for stabilizing organic material against oxidative, thermal or actinic degradation which comprises incorporating therein or applying thereto an effective stabilizing amount of the compound of formula I

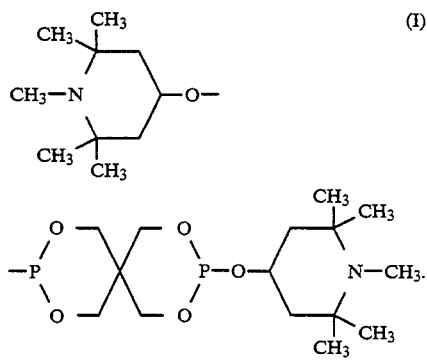

10. A process according to claim 9 for stabilising thermoplastic polymers against oxidative and thermal degradation during processing.

* * * * *